(12) United States Patent
Clarke

(10) Patent No.: US 11,571,479 B2
(45) Date of Patent: *Feb. 7, 2023

(54) NUTRITIONAL COMPOSITION

(71) Applicant: TDELTAS LIMITED, Thame (GB)

(72) Inventor: Kieran Clarke, Oxford (GB)

(73) Assignee: TDELTAS, Thame (GB)

( * ) Notice: Subject to any disclaimer, the term of this patent is extended or adjusted under 35 U.S.C. 154(b) by 0 days.

This patent is subject to a terminal disclaimer.

(21) Appl. No.: 16/881,597

(22) Filed: May 22, 2020

(65) Prior Publication Data

US 2020/0360517 A1 Nov. 19, 2020

Related U.S. Application Data

(63) Continuation of application No. 13/580,602, filed as application No. PCT/EP2011/000833 on Feb. 22, 2011, now Pat. No. 10,660,958.

(30) Foreign Application Priority Data

Feb. 22, 2010 (GB) .................................... 1002983

(51) Int. Cl.

| | |
|---|---|
| A61K 31/22 | (2006.01) |
| A01N 37/02 | (2006.01) |
| A61K 47/06 | (2006.01) |
| A23C 9/154 | (2006.01) |
| A23L 2/39 | (2006.01) |
| A23L 2/56 | (2006.01) |
| A61K 9/00 | (2006.01) |
| A23L 33/00 | (2016.01) |
| A23L 33/10 | (2016.01) |
| A23L 33/175 | (2016.01) |
| A23L 27/00 | (2016.01) |

(52) U.S. Cl.
CPC ............ *A61K 47/06* (2013.01); *A23C 9/1544* (2013.01); *A23L 2/39* (2013.01); *A23L 2/56* (2013.01); *A23L 27/00* (2016.08); *A23L 33/10* (2016.08); *A23L 33/175* (2016.08); *A23L 33/40* (2016.08); *A61K 9/0095* (2013.01); *A61K 31/22* (2013.01)

(58) Field of Classification Search
CPC .......... A61K 47/06; A61K 9/00; A61K 31/22; A23C 9/154; A23L 2/39; A23L 33/00; A23L 33/10; A23L 27/00; A32L 2/56
USPC ....................................................... 514/546
See application file for complete search history.

(56) References Cited

U.S. PATENT DOCUMENTS

| | | | |
|---|---|---|---|
| 3,984,566 A | 10/1976 | Van Scott et al. | |
| 4,380,549 A | 4/1983 | Van Scott et al. | |
| 5,112,865 A | 5/1992 | Nichels et al. | |
| 5,126,373 A † | 6/1992 | Brunengraber | |
| 5,281,691 A | 1/1994 | Hubbs et al. | |
| 5,654,266 A | 8/1997 | Chen et al. | |
| 5,665,831 A | 9/1997 | Neuenschwander et al. | |
| 5,693,850 A | 12/1997 | Birkhahn et al. | |
| 6,126,953 A | 10/2000 | Costa et al. | |
| 6,136,862 A | 10/2000 | Hiraide et al. | |
| 6,207,856 B1 | 3/2001 | Veech | |
| 6,316,038 B1 | 11/2001 | Veech | |
| 6,323,237 B1 | 11/2001 | Veech | |
| 6,380,244 B2 | 4/2002 | Martin et al. | |
| 6,544,960 B1 | 4/2003 | Eldred et al. | |
| 6,939,570 B1 | 9/2005 | Snow et al. | |
| 7,351,736 B2 | 4/2008 | Veech | |
| 8,101,653 B2 | 1/2012 | Veech | |
| 8,642,654 B2 | 2/2014 | Clarke | |
| 9,034,613 B2 | 5/2015 | Robertson et al. | |
| 9,211,275 B2 | 12/2015 | Clarke et al. | |
| 2001/0041736 A1 † | 11/2001 | Veech | |
| 2001/0047008 A1 | 11/2001 | Baraldi | |
| 2002/0006959 A1 | 1/2002 | Henderson | |
| 2002/0013339 A1 | 1/2002 | Martin et al. | |
| 2002/0035231 A1 | 3/2002 | Whitehouse et al. | |
| 2004/0063661 A1 | 4/2004 | Linnane | |
| 2004/0171671 A1 | 9/2004 | Veech | |
| 2004/0266872 A1 | 12/2004 | Veech et al. | |
| 2005/0129783 A1 | 6/2005 | McCleary et al. | |
| 2006/0078596 A1 | 4/2006 | Clarke et al. | |
| 2006/0189545 A1 † | 8/2006 | Henderson | |

(Continued)

FOREIGN PATENT DOCUMENTS

| | | |
|---|---|---|
| CA | 1330307 C | 6/1994 |
| CA | 2173270 A | 10/1996 |

(Continued)

OTHER PUBLICATIONS

Mayo Clinic 1998.*

(Continued)

*Primary Examiner* — Shirley V Gembeh
(74) *Attorney, Agent, or Firm* — Brian C. Trinque; Lathrop GPM LLP

(57) ABSTRACT

An organoleptically acceptable composition containing a ketone body or a ketone body precursor including a hydroxybutyrate ester and a flavouring is provided and gives improved palatability and user adherence to the intended dose regime. The flavouring may be a bitter flavouring and the composition may further contain an adsorbent for the ketone such that on ingestion, the bitterness of the composition may be masked. The composition may be in the form of a solid, gel or liquid and provides increased blood ketone levels and may be used in therapy or in treating muscle impairment or fatigue.

19 Claims, 2 Drawing Sheets

(56) References Cited

U.S. PATENT DOCUMENTS

| | | | |
|---|---|---|---|
| 2006/0280721 | A1† | 12/2006 | Veech |
| 2007/0179197 | A1 | 8/2007 | Henderson |
| 2008/0287372 | A1 | 11/2008 | Henderson et al. |
| 2009/0197952 | A1 | 8/2009 | Hashim et al. |
| 2009/0253781 | A1 | 10/2009 | Veech |
| 2010/0298294 | A1 | 11/2010 | Clarke et al. |
| 2011/0237666 | A1 | 9/2011 | Clarke et al. |
| 2012/0064611 | A1 | 3/2012 | Robertson et al. |
| 2012/0071548 | A1 | 3/2012 | Veech |
| 2012/0213835 | A1 | 8/2012 | Neas et al. |
| 2013/0102663 | A1 | 4/2013 | Clarke et al. |
| 2014/0194509 | A1 | 7/2014 | Clarke et al. |
| 2014/0308719 | A1 | 10/2014 | Clarke et al. |
| 2015/0065571 | A1 | 3/2015 | Clarke et al. |
| 2015/0164855 | A1 | 6/2015 | Clarke et al. |
| 2015/0250755 | A1 | 9/2015 | Veech et al. |

FOREIGN PATENT DOCUMENTS

| | | | |
|---|---|---|---|
| CN | 1483355 | A | 9/2002 |
| CN | 1552315 | A | 12/2004 |
| DE | 20205184 | U | 12/2002 |
| EP | 0 552 896 | A1 | 7/1993 |
| EP | 1 568 780 | A1 | 8/2005 |
| EP | 1 809 235 | B1 | 7/2007 |
| GB | 1524611 | A | 9/1978 |
| GB | 2511941 | A | 9/2014 |
| JP | S54-138126 | A | 10/1979 |
| JP | S63-112998 | A | 5/1988 |
| JP | H01-095730 | A | 4/1989 |
| JP | H01-160917 | A | 6/1989 |
| JP | H03-083950 | A | 4/1991 |
| JP | H04-112825 | A | 4/1992 |
| JP | H07-076513 | A | 3/1995 |
| JP | H10-175855 | A | 6/1998 |
| JP | H10-265378 | A | 10/1998 |
| JP | 2005247821 | A | 9/2005 |
| JP | 2008127369 | A | 6/2008 |
| JP | 2009532496 | A | 9/2009 |
| JP | 2012500264 | A | 1/2012 |
| SU | 507322 | A | 3/1976 |
| WO | 1987003806 | A1 | 7/1987 |
| WO | 1995009144 | † | 4/1995 |
| WO | 1995009144 | A1 | 4/1995 |
| WO | 1998041200 | A1 | 9/1998 |
| WO | 2000004895 | A1 | 2/2000 |
| WO | 2000015216 | A1 | 3/2000 |
| WO | 2001013877 | A1 | 3/2001 |
| WO | 2001051645 | A1 | 7/2001 |
| WO | 2004105742 | A1 | 12/2004 |
| WO | 2004108740 | A1 | 12/2004 |
| WO | 2006020137 | A2 | 2/2006 |
| WO | 2006061624 | A1 | 6/2006 |
| WO | 2006070337 | A2 | 7/2006 |
| WO | 2007001883 | A2 | 1/2007 |
| WO | 2007063037 | A2 | 6/2007 |
| WO | 2007115282 | A2 | 10/2007 |
| WO | 2007115934 | A1 | 10/2007 |
| WO | 2008119032 | A1 | 10/2008 |
| WO | 2008140828 | A1 | 11/2008 |
| WO | 2009023357 | A2 | 2/2009 |
| WO | 2010021766 | A1 | 2/2010 |
| WO | 2010120300 | A1 | 10/2010 |
| WO | 2011101171 | A1 | 8/2011 |
| WO | 2011121540 | A1 | 10/2011 |
| WO | 2012113415 | A1 | 8/2012 |
| WO | 2014071389 | A1 | 5/2014 |

OTHER PUBLICATIONS

Mancuso et al. Neuromuscular Disorders 22(2012)S226-S229.*
Schulte-Mattler Arch Neurol. 2003;60:50-58.*
"Drug Therapy of Dyslipidemia" in Goodman & Gilman's The Pharmacological Basis of Therapeutics, 11th Ed., McGraw-Hill (New York), pp. 948-953 (2006).
Abdelwahab et al. (2012) "The Ketogenic Diet Is an Effective Adjuvant to Radiation Therapy for the Treatment of Malignant Glioma," PLOS ONE. 7(5):E36197. pp. 1-7.
Boyarinov et al. (1984) "Effect of Sodium hydroxybutyrate on myocardial high-energy phosphates, function, and ultrastructure after blood loss", Biulleten' eksperimental'noT biologii i meditsiny. 97(3):289-292.
Buteau (2009) "Obviousness of Enantiomers over Prior Art Racemates," The Journal of High Technology Law. L22. pp. 42-49.
Clark et al. (2005) "Dilated Cardiomyopathy and Acute Liver Injury Associated with Combined Use of Ephedra, yHydroxybutyrate, and Anabolic Steroids" Pharmacotherapy. 25(5):756-761.
Davey et al. (1988) "Radioprotection of rat subependymal plate with 4-0H sodium butyrate," NCI Monogr. (6):231-234.
Desrochers et al. (1992) "Metabolism of R and S-1 ,3-butanediol in perfused livers from meal-fed and starved rats," Biochem. J. 285:647-653.
Desrochers et al. (1995) "Metabolism of {R,S)-1 ,3-butanediol acetoacetate esters, potential parenteral and enteral nutrients in conscious pigs," Am. J. Physiol. 268:E660-667.
Desrochers et al. (1995) "R, S-1, 3-butanediol acetoacetate esters, potential alternates to lipid emulsions for total parenteral nutrition," Journal of Nutritional Biochemistry. 6(2):111-118.
Eagles et al. (1997) "The effects of combined treatment with β1-selective receptor antagonists and lipid-lowering drugs on fat metabolism and measures of fatigue during moderate intensity exercise: a placebo-controlled study in healthy subjects," Brit. J. Clinical Pharmacol. 43:291-300.
Edegger et al. (2006) "Regia- and Stereoselective Reduction of Diketones and Oxidation of Dials by Biocatalytic Hydrogen Transfer," Eur. J. Org. Chem. 2006(8):1904-1909.
Felig et al. (1971) "Amino acid metabolism in exercising man." J. Clin. Invest. 50(12):2703-2714.
Goldbort et al. (1976) "Butanediols: Selection, open field activity, and NAD reduction by liver extracts in inbred mouse strains," Pharmacology Biochemistry and Behaviour. 5(3):263-268.
Kalaitzakis et al. (2005) "Highly Stereoselective Reductions of a-Aikyl-1 ,3-diketones and a-Aikyi-Jl-keto Esters Catalyzed by Isolated NADPH-Dependent Ketoreductases," Org. Lett. 7(22):4799-4801.
Kashiwaya et al. (2013) "A ketone ester diet exhibits anxiolytic and cognition-sparing properties, and lessens amyloid and tau pathologies in a mouse model of Alzheimer's disease," Neurobiology of Aging. 34(6):1530-1539.
Kohut et al. (1995) "Effects of decresased free fatty acids on fatigue during exercise with carbohydrate feedings," Medicine and Science in Sports & Exercise. 27(5 Suppi):S102.
Kulinskii et al. (1993) "The radioprotective effect of GABA-tropic substances, gamma-hydroxybutyrate and piracetam," Radiobiologiia. 33(1):133-136.—English Abstract Only.
Larios et al. "Synthesis of flavor and fragrance esters using Candida antarctica lipase," Appl. Microbiol. Biotechnol. (2004) 65: 373-376.
Mori et al. (1987) "New synthesis of both enantiomers of grandisol, the boll weevil pheromon," Tetrahedron. 43 (10):2229-2239.
Nair et al. (1988) "Effect of beta-hydroxybutyrate on whole-body leucine kinetics and fractional mixed skeletal muscle protein synthesis in humans," J. Clin. Invest. 82(1 ):198-205.
Neubauer et al. (1997) "Myocardial Phosphocreatine-to-ATP Ratio is a predictor of mortality in patients with dilated cardiomyopathy," Circulation. 96:2190-2196.
Ostrovskaya et al. (1981) "Effect of prolonged administration of sodium hydroxybutyrate on the working capacity and muscle tissue in rats," Farmakologiya I Toksikologiya. 44(5):534 539.—Only English Abstract Provided.
Puchowicz et al. (2000) "Dog model of therapeutic ketosis induced by oral administration of R,S-1 ,3-butanediol diacetoacetate," J. Nutr. Biochem. 11:281-287.
Rossi et al. (2000) "Suppression of Feed Intake after Parenteral Administration of D-1313-Hydroxybutyrate in Pygmy Goats," J. Vet. Med. A. 47:9-16.

(56) References Cited

OTHER PUBLICATIONS

Shaw et al. (1984) "Influence of beta-hydroxybutyrate infusion on glucose and free fatty acid metabolism in docs," Am. J. Phys. 247:E756-764.
Sherwin et al. (1975) "Effect of ketone infusions on amino acid and nitrogen metabolism in man" J. Clin. Invest. 55(6) 1382-1390.
Simons et al. (1982) "Long term treatment with Slow Release Oxprenolol Alone, or in Combination with other Drugs: Effects on Blood Pressure, Lipoproteins and Exercise Performance," Aust. N. Z. J. Med. 12:612-616.
Smith et al. (1975) "Initial effect of injury on ketone bodies and other blood metabolites," Lancet. 1(7897):1-3.
Tobin et al., (1972) "Effect Of 1,3-Butanediol and Propionic Acid on Blood Ketones, lipids d Metal Ions in Rats", Journal of Nutrition, vol. 102, No. 8, 1972, pp. 1001-1008.
Turner et al. (1999) "Glycemic control with diet, sulfonylurea, metformin, or insulin in patients with type 2 diabetes mellitus: progressive requirement for multiple therapies (UKPDS 49)." JAMA. 281(21):2005-2012.
Wu et al. (1987) "Ketone bodies inhibit leucine degradationin chick skeletal muscle," International J. of Biochem. 19 (10):937-943.
Zhu et al. (2006) "A recombinant ketoreductase tool-box. Assessing the substrate selectivity and stereoselectivity toward the reduction of Jl-ketoesters," Tetrahedron. 62:901-905.
International Preliminary Report on Patentability corresponding to International Patent Application No. PCT/US2009/040773, dated Oct. 18, 2011.
International Prelminary Report on Patentablility corresponding to International Patent Application No. PCT/US2009/030095, dated Jul. 6, 2010.
International Search Report corresponding to International Patent Application No. PCT/EP2013/069189, dated Aug. 12, 2014.
International Search Report corresponding to International Patent Application No. PCT/EP2014/055158, dated Jun. 25, 2014.
International Search Report corresponding to International Patent Application No. PCT/US2009/030095, dated Feb. 23, 2009.
International Search Report with Written Opinion corresponding to International Patent Application No. PCT/EP2013/057250, dated Jun. 11, 2013.
International Search Report with Written Opinion corresponding to International Patent Application No. PCT/EP2014/067027, dated Oct. 30, 2014.
International Search Report with Written Opinion corresponding to International Patent Application No. PCT/GB2004/002286, dated Oct. 11, 2004.
International Search Report with Written Opinion corresponding to International Patent Application No. PCT/US2004/018016, dated Apr. 15, 2005.
International Search Report with Written Opinion corresponding to International Patent Application No. PCT/US2013/068545, dated Jan. 20, 2014.
International Search Report with Written Opinion corresponding to Interntational Patent Application No. PCT/US2009/040766, dated Aug. 6, 2009.
International Search Report with Written Opinion corresponding to Interntational Patent Application No. PCT/US2009/040773, dated Feb. 22, 2010.
Supplementary European Search Report and Written Opinion corresponding to European Patent Application No. 09701051.6, dated Jan. 19, 2011.
Search and Examination Report corresponding to Great Britain Patent Application No. 1404400.2, dated Mar. 26, 2014.
Search and Examination Report corresponding to Great Britain Patent Application No. 1404577.7, dated Oct. 23, 2014.
Search and Examination Report corresponding to Great Britain Patent Application No. 1414016.4, dated Aug. 29, 2014.
Search Report corresponding to Great Britain Patent Application No. 1002983.3, dated Jun. 10, 2010.
International Search Report & Written Opinion from PCT/EP2011/000833, dated Jun. 22, 2011.

\* cited by examiner
† cited by third party

NUTRITIONAL COMPOSITION

CROSS REFERENCE TO RELATED APPLICATIONS

This application is a continuation of U.S. patent application Ser. No. 13/580,602, filed on Jan. 4, 2013, now U.S. Pat. No. 10,660,958, which application is a national phase entry of International Application No. PCT/EP11/00833, filed on Feb. 22, 2011, which claims priority to GB Patent Application No. 1002983.3, filed Feb. 22, 2010, each of which is incorporated herein in its entirety.

This invention relates to a nutritional composition, especially to an organoleptically acceptable composition comprising a ketone body, a process for production of the composition and use of the composition in raising the circulating ketone concentrations in the blood plasma of a subject.

Ketone bodies are produced when fatty acids levels are raised in the body and are metabolised by the body for energy. Ketone bodies have been disclosed as being suitable for reducing the levels of free fatty acids circulating in the plasma of a subject and that ingestion of ketone bodies can lead to various clinical benefits, including an enhancement of physical and cognitive performance and treatment of cardiovascular conditions, diabetes and treatment of mitochondrial dysfunction disorders and in treating muscle fatigue and impairment.

WO2004/108740 discloses compounds and compositions containing (R)-3-hydroxybutyrate derivatives effective for elevating blood concentrations of ketone bodies and methods for using such compounds and compositions as nutritional supplements or for treating medical conditions. (R)-3-hydroxybutyrate derivatives and compositions that include these derivatives may serve as precursors to ketone bodies, such as acetoacetate and (R)-3-hydroxybutyrate, and are said to yield elevated blood concentrations of ketone bodies when administered to a subject.

WO2004/105742 discloses the use of a compound for example ketone bodies, salicylic acid, nicotinic acid, thiazolidine diones and fibrates, that reduces free fatty acids circulating in the blood plasma of a subject for the treatment or prevention of muscle, particularly cardiac or skeletal muscle impairment or fatigue or mitochondrial dysfunction. Liquid compositions for rehydration during or after exercise, comprising water, a sugar carbohydrate and a compound that reduces free fatty acids circulating in blood plasma are also disclosed.

However, whilst certain therapeutic and other benefits of ketone bodies are known, they are generally unpalatable and have strongly negative organoleptic properties, especially ketone esters. Provision of sufficient ketone body to provide beneficial effects is accordingly problematic and consumption of ketones and their esters is generally not known as a part of a conventional diet due to their highly unpalatable taste. As a consequence, adherence of a user or patient to an appropriate dosage regimen or in ensuring patient compliance may be very difficult.

To gain desirable therapeutic and other benefits, the ketone body generally needs to be present in the blood plasma at a threshold level, for example at least 1 mM, and difficulties are encountered in ensuring ingestion of sufficient ketone body to provide the desired blood plasma levels to provide the desired effect. A need exists to provide a less unpalatable means of delivering the desired ketone bodies to the user at a sufficiently high level to provide the desired effects.

Provision of a formulation which has acceptable shelf life and product stability and is readily consumable directly or in combination with a liquid carrier, for example water, would also be desirable.

We have now found that by selecting a certain combination of components including a ketone body containing a hydroxybutyrate ester and a flavouring, especially a bitter flavouring, an organoleptically acceptable composition which allows ketone to pass into the blood plasma at a desirable level may be obtained.

Figure 1:
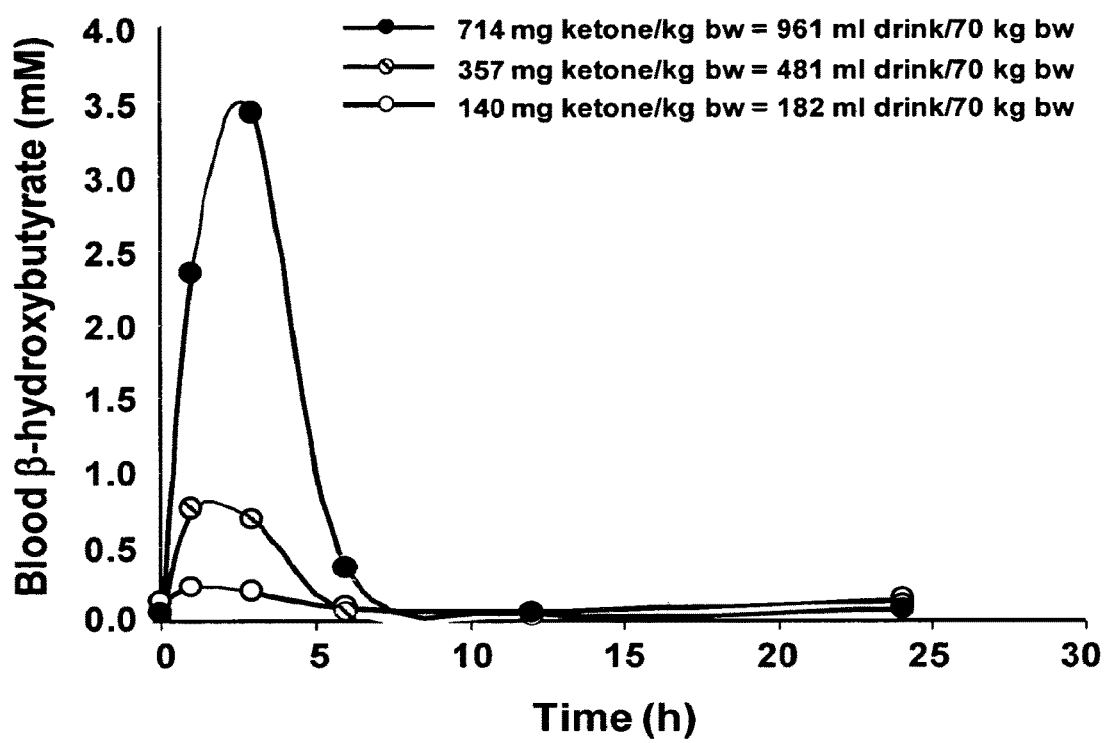
FIG. 1 is a graph depicting the blood beta-hydroxybutyrate concentrations of human subjects following administration of a composition to the disclosure.

The invention provides in a first aspect an organoleptically acceptable composition comprising a ketone body or a ketone body precursor including a hydroxybutyrate ester, a flavouring and optionally one or more of a protein, carbohydrate, sugars, fat, fibre, vitamins and minerals.

As used herein, the term "ketone", "ketone body" or "ketone bodies" means a compound or species which is a ketone or a ketone body precursor, that is, a compound or species which is a precursor to a ketone and which may be converted or metabolised to a ketone. The present invention requires the presence of a hydroxybutyrate ester as part of or the whole of the ketone body or its precursor.

By "organoleptically acceptable" we mean that the composition must possess acceptable sensory properties of taste, colour, feel and odour. The organoleptic acceptability or otherwise of the composition is a subjective assessment by the user having regard to external factors including personal taste. In the present invention, organoleptically acceptability is determined by conducting taste surveys utilising a sample population of volunteers in a blind test, for example as set out in Example 9 herein.

The invention also provides an organoleptically acceptable product comprising a composition according to the invention and instructions for a dosage regime for consumption of the composition such that the user ingests at least 100 mg per kilogram of body weight of ketone per day wherein the composition comprises a ketone at a level of up to 50% and on consumption of the composition according to the instructions, provides a blood plasma ketone level of at least 0.1 mM, preferably at least 0.2 mM, more preferably at least 1 mM and optimally at least 3 mM.

Suitably the composition is ingested at a level such that the blood plasma ketone level does not exceed 8 mM and desirably does not exceed 5 mM.

The blood plasma level of ketone will depend on the body mass of the individual and we have found that a ketone dose of at least 300 mg of ketone per kilogram of body weight provides a blood plasma concentration of ketone of around 1.5 mM.

Blood plasma levels of ketone may be determined by commercially available testing kits, for example, Ketostix, available from Bayer, Inc.

Suitably the instructions for consumption comprise instructions to consume one or more doses of a composition according to the invention per day. A single daily dose provides the advantage of a greater likelihood of user compliance with the dosing regime. Advantageously, the daily intake of the composition is consumed in a plurality of doses to provide a more even ketone concentration than provided in a single dose. Preferably at least 2 doses, more preferably 2 to 8 doses for example 3 or 6 doses are consumed daily. Suitably the doses are consumed at regular intervals as this maintains a more even level of blood ketone content although a user may consume a dose of the composition prior to anticipated fatigue or possible reduced cognitive function so as to "prime" the blood with ketone to mitigate the advent of fatigue or cognitive impairment.

The invention further comprises a method of administration of a ketone body or a ketone body precursor in a dose regime wherein the regime comprises administering in at least one dose per day an organoleptically acceptable composition comprising the ketone body or ketone body precursor in an amount of at least 100 mg per kg of bodyweight per dose and preferably at least 300 to 750 mg/kg.

The level of ketone body in the composition suitably differs depending on whether the composition is in solid form or liquid form. Where the composition is in solid form, it suitably comprises at least 5% by weight of ketone body including the hydroxybutyrate ester, more preferably at least 10% by weight and up to 95% by weight of the composition. Whilst a level of 15 to 30% by weight of the dry composition may be suitable, for example where the composition is a dry powder intended for use with a liquid to produce a liquid composition, a solid bar or product form suitably comprises from 30 to 95%, especially 50 to 95% by weight of the composition. Where the composition is in liquid form, the composition suitably comprises the ketone body at a level of at least 1%, for example 3 to 7% by weight of the liquid composition but may be higher for example up to 50% by weight of the composition depending on whether the composition is intended to be taken as a single dose or in multiple smaller doses to reach the desired blood ketone level.

The composition in liquid form suitably comprises the dry composition diluted with a suitable liquid, for example water, fruit juice or milk, preferably at a ratio of 1:1 to 1:10, more preferably 1:3 to 1:7 of dry composition to liquid. The level of ketone body which is organoleptically acceptable will vary according to the precise composition and its form and the masking effect of other components of the composition.

The bitterness of ketone bodies and especially ketone esters means that as the level of ketone body in the composition increases, there is a heightened risk that the user will find the composition unacceptably unpalatable. The level of ketone in the composition is accordingly selected according to the context and having regard to the risk of non-compliance with the intended dosing regimen.

We have found that ketone esters are digested more effectively than other forms of ketone for example triolides and oligomers. In order to benefit from the relative ease of digestion, the ketone body preferably comprises a ketone ester. As a practical benefit, to achieve a given level of plasma ketone, the composition may contain a lower level of ketone ester than if another ketone body were to be used, so allowing more desirable formulation in order to achieve a given blood plasma ketone level. Preferably, the ketone ester comprises a partial ester, that is a polyol in which only a proportion of the hydroxyl groups are esterified. Monoesters are especially preferred and esters where two or more hydroxyl groups have been esterified but the esterified hydroxyl groups are not in a "beta-relationship, that is in which the hydroxyl groups are not attached to adjacent carbon atoms.

The composition is preferably consumed in sufficient quantities to provide an average daily intake of at least 5 g of ketone body per day, preferably from 20 to 200 g of ketone body per day. This may be taken in a small number of doses but, more preferably in a higher number of doses with a lower quantity of ketone in each dose so as to be less unpalatable, as desired.

Ketone esters have nonetheless still been found generally to be bitter to the human taste so whilst they are beneficial as regards ease of digestion it remains desirable to mitigate their negative organoleptic properties further. We have found ketone monoesters to be less bitter than other esters and the ketone ester preferably comprises a ketone monoester.

The level of ketone body which is organoleptically acceptable will vary according to the precise composition and its form and the masking effect of other components of the composition. The composition may be solid, for example a powder, tablet, bar, confectionary product or a granule and intended for use as a solid oral dose form. In another embodiment, the solid composition may be mixed before use with a liquid, preferably water, fruit based liquid or a dairy product for example milk and yogurt, to provide a liquid drink for the user. Milk, fruit juice and water are especially preferred as a carrier for the composition. The composition may be provided, as desired, as a liquid product in a form ready for consumption or as a concentrate or paste suitable for dilution on use. The diluent for use with the liquid composition is preferably milk, fruit juice or water.

The composition may also be provided in encapsulated form provided that the encapsulation material and the quantity in which it is used is suitable for safe human consumption. However, encapsulation is not preferred.

Any ketone body may be employed in the composition or any compound which provides a ketone in the human body. Preferably, a ketone ester is employed and especially a ketone monoester. Examples of suitable ketone bodies or compounds which provide a ketone body in situ include hydroxybutyrates and derivatives thereof, for example esters of hydroxybutyrate including (R)-3-hydroxybutyrate and derivatives thereof, esters of (R)-3-hydroxybutyrate and oligomers of (R)-3-hydroxybutyrate including esters derived from alcohols and compounds containing one or more free hydroxyl groups. Suitable alcohols include butanediol, especially, butane-1,3-diol, altrose, arabinose, dextrose, erythrose, fructose, galactose, glucose, glycerol, gulose, idose, lactose, lyxose, mannose, ribitol, ribose, ribulose, sucrose, talose, threose, xylitol, xylose. In an especially preferred embodiment, the ketone comprises 3-hydroxybutyl-(R)-3-hydroxybutyrate, particularly in enantiomerically enriched form.

We have found that certain ketone bodies exhibit bitterness including those resulting from esterification of a chain of 2 or 3 beta-hydroxybutyrate groups on an alcohol leads to bitter taste, for example a butandiol triolide diester, fructose esterified on 4 hydroxy with dimers of beta-hydroxybutyrate, glycerol esterfied with 2 beta-hydroxybutyrate groups on one hydroxyl and butandiol esterified with 2 beta-hydroxybutyrate groups on one hydroxyl. We have also found that esterification of adjacent hydroxyls with beta-hydroxybutyrate groups leads to bitterness for example glycerol esterified with 1 beta-hydroxybutyrate on each of the three hydroxyls.

We have also found that an unpleasant taste although less or no bitter taste results from esterification of 1 beta-hydroxybutyrate on the 2 non-adjacent hydroxyls of butandiol. We have also found that non-aversive "clinical taste" resulted from esterification of 1 beta-hydroxybutyrate on one hydroxyl of 1,3 butandiol and from esterification of 1 beta-hydroxybutyrate on one of the 3 hydroxyls of glycerol although this provided a more "clinical taste". These ketone bodies are preferred.

D-β-hydroxybutyrate-R 1,3-butanediol monoester is especially preferred. D-β-hydroxybutyrate-R 1,3-butanediol monoester may be employed in combination with other ketone bodies or ketone body precursors in an amount less than any other such ketone bodies or preferably in an amount more than any such other ketone body. In an especially preferred embodiment D-β-hydroxybutyrate-R 1,3-butanediol monoester is the only ketone body or ketone body precursor present in the composition of the invention.

Suitably, the composition is substantially free of ketone bodies or ketone body precursors other than a ketone monoester and preferably is substantially free of ketone bodies or ketone body precursors other than a D-β-hydroxybutyrate monoester and more preferably is substantially free of ketone bodies or ketone body precursors other than a D-β-hydroxybutyrate-R 1,3-butanediol monoester.

Other low bitter or tasteless forms of beta-hydroxybutyrate esters include linear oligomers of beta-hydroxybutyrate and ethanol ester of beta-hydroxybutyrate which is undesirable due to the effects of ethanol on cognitive function and anticipated decreased physiological performance resulting from its metabolic product acetate. Mono esters of beta-hydroxybutyrate with alcohols which are unlikely to cause untoward physiological effects if feed in high amounts, for example glucose monoesters and glycerol monoesters and R 1,3 butandiol monoesters are preferred.

Linear oligomers of beta-hydroxybutyrate of lower monomer size, for example from 1 to 9, may be toxic and mixtures centering on 9 or 10 mer length are generally not absorbable from the gut and so are undesirable.

Composition of the invention may contain a medium chain triglyceride (MCT) and optionally their associated fatty acids. MCTs comprise fatty acids with a chain length of between 5 and 12 carbon atoms. It is known that a diet rich in MCT results in high blood ketone levels. Suitable medium chain triglycerides are represented by the following formula $CH_2R_1—CH_2R_2—CH_2R_3$ wherein R1, R2 and R3 are fatty acids having 5 to 12 carbon atoms. Preferably, MCTs wherein R1, R2, and R3 are fatty acids containing a six-carbon backbone (tri-C6:0) are employed as it is reported that tri-C6:0 MCT are absorbed very rapidly by the gastrointestinal track.

Where an MCT is employed, suitably the composition of the invention comprises i) a ketone body, preferably a ketone monoester, more preferably a D-β-hydroxybutyrate monoester and ii) a MCT, preferably tri-C6:0 MCT.

The composition of the invention may also comprise L-carnitine or a derivative of L-carnitine.

Examples of derivatives of L-carnitine include decanoyl-carnitine, hexanoylcarnitine, caproylcarnitine, lauroylcarnitine, octanoylcarnitine, stearoylcarnitine, myristoylcarnitine, acetyl-L-carnitine, O-Acetyl-L-carnitine, and palmitoyl-L-carnitine.

Where a carnitine is employed, suitably the composition of the invention comprises i) a ketone body, preferably a ketone monoester, more preferably a D-β-hydroxybutyrate monoester and ii) L-carnitine or a derivative of L-carnitine.

In a further embodiment, the composition may comprise i) a ketone body, preferably a ketone monoester, more preferably a D-β-hydroxybutyrate monoester ii) a MCT, preferably tri-C6:0 MCT or a tri-C8:0 MCT and iii) L-carnitine or a derivative of L-carnitine.

Where MCT and L-carnitine or its derivative is employed, suitably the MCT is emulsified with the carnitine. Preferably 10 to 500 g of emulsified MCT is combined with 10 to 2000 mg of carnitine for example 50 g MCT (95% triC8:0) emulsified with 50 g of mono- and di-glycerides combined with 500 mg of L-carnitine.

The MCT may be present in a greater amount than the ketone body but preferably the level of ketone body is greater than the level of the MCT.

The composition suitably comprises one or more components selected from milk powder, maltodextrin and sugar to provide a protein source and a sweetener to assist in masking the flavour of the ketone body. Depending on the components selected the level of protein may be reduced or dispensed with, for example where mango is employed to act as a sweetener, milk powder is not required to provide an organoleptically acceptable composition.

The composition further comprises a flavouring. Suitably the flavouring assists in providing a palatable product and may be selected according to market requirements and local tastes. Examples of suitable flavourings include strawberry, banana, caramel and raspberry.

We have found that especial benefit as regards organoleptic properties may be achieved by employing a bitter flavouring. Without being bound by any theory, it is believed that the user expectation and taste associated with a bitter flavour assists in rendering the perception of the composition as being less bitter hence improving the palatability of the composition and reducing the risk of non-compliance with the dosing regime.

Bitter flavourings are preferred for example liquorice, coffee, chocolate and cranberry, as these have been found to provide effective masking of the ketone body.

The composition may comprise one or more of a protein, for example a whey protein isolate, nutriose FB06, vitamin and mineral premix and fibre. In a preferred fully formulated product, the composition comprises, in addition to the ketone, protein, carbohydrate, fat, fibre, vitamins, minerals, sweetener and flavouring sufficient to render the composition palatable.

Suitably the ketone body provides at least 10%, preferably at least 20% and desirably 25 to 35% of the calorific value of the composition.

Preferably the composition comprises protein at a level of at least 5% by weight of the composition, more preferably at least 10%. Desirably, the protein is a present at a level of not more than 95% by weight of the composition, more desirably not more than 50% by weight.

Preferably the composition comprises carbohydrate at a level of at least 30%, preferably at least 40% by weight of the composition. Desirably, the carbohydrate is a present at a level of not more 95% by weight of the composition, more desirably not more than 50% by weight.

Preferably the composition comprises sugar or sweetener at a level of at least 15%, preferably at least 25% by weight of the composition. Desirably, the sugar or sweetener is a present at a level of not more than 95% by weight of the composition, more desirably not more than 50% by weight.

Preferably the composition comprises fat at a level of at least 5%, preferably at least 10% by weight of the composition. Desirably, the fat is a present at a level of not more than 95% by weight of the composition, more desirably not more than 50% by weight.

Preferably the composition comprises fibre at a level of at least 2%, preferably of at least 4% by weight of the composition. Desirably, the fat is a present at a level of not more than 95% by weight of the composition, more desirably not more than 50% by weight.

The composition preferably also comprises vitamins and minerals at a level such that at least 50%, more preferably at least 80% and desirably 100% of the recommended daily allowance is provided on consumption of the composition according to a recommended dosage regime over a 24 hour period. For example, if the recommended regime stipulates that the composition is to be consumed in five doses over a period of 24 hours, each dose will comprises up to 20% of the recommended daily allowance for vitamins and minerals.

The composition suitably comprises components known to those skilled in the art to improve the sensory perception, for example texture of the composition on consumption. Suitable components include gums, emulsifiers, stabilisers and the like.

When the composition is in solid form the composition may further comprise one or more of the following components:
    a diluent for example lactose, dextrose, saccharose, cellulose, corn starch or potato starch;
    a lubricant for example silica, talc, stearic acid, magnesium or calcium stearate and/or polyethylene glycols;
    a binding agent for example starches, arabic gums, gelatin, methylcellulose, carboxymethylcellulose, or polyvinyl pyrrolidone;
    a disintegrating agent such as starch, alginic acid, alginates or sodium starch glycolate;
    an effervescing agent;
    a dyestuff;
    a sweetener;
    a wetting agent for example lecithin, polysorbates, lauryl sulphates.

In a preferred embodiment of the invention, the composition comprises an adsorbent which is pharmaceutically acceptable. Suitably the adsorbent adsorbs the ketone body or a ketone body precursor including a hydroxybutyrate ester, containing ketone body or a ketone body precursor including a hydroxybutyrate ester in or the adsorbent such that the undesirable flavour of the ketone body or a ketone body precursor is experienced to a lesser degree by the user than would be experienced on consumption of the same composition without the adsorbent. Preferably the adsorbent comprises a lattice or voids capable of retaining the ketone body or a ketone body precursor including a hydroxybutyrate ester.

Any adsorbents used or known for use in food products may be employed to mitigate the undesirable flavour of the ketone body or a ketone body precursor including a hydroxybutyrate ester. Examples of suitable adsorbents include a polymer hydrogel, for example a polymer of a crosslinked polycarboxylate homopolymer or copolymer, a clathrate, a cyclic oligosaccharide, for example cyclodextrins, and milk powder.

The adsorbent may also provide a nutritional function, for example providing a source of protein, and the composition may contain a component, for example milk powder which provides both a source of protein and an adsorbent function.

The adsorbent may be present at any desired level according to the particular formulation and may be from 5% to 80% by weight of the composition, for example from 10 to 50%.

Suitably, the ketone body or a ketone body precursor including a hydroxybutyrate ester is adsorbed into the adsorbent upon manufacture and the inventors have found that for a given composition of the invention containing an adsorbent, the perceived level of bitterness decreases over a period of time, for example at least 1 week, at least 1 month and at least 3 months after production of the composition.

The invention provides in a further aspect a method of producing an organoleptically acceptable composition comprising a ketone body or a ketone body precursor including a hydroxybutyrate ester, a flavouring and an adsorbent which comprises including an adsorbent in a composition of the invention and storing the composition comprising the adsorbent for a period of at least 1 week.

The perceived level of bitterness is suitably determined on a qualitative, quantitative or semi-quantitative basis, for example by employing a testing panel as set out in Example 9 below.

The composition may suitably be manufactured in a known manner, for example by means of mixing, granulating, agglomeration, tableting, sugar coating, or film-coating processes.

The composition may be in the form of a solid or in the form of a liquid composition or a gel.

Suitable solid forms of the composition include a bar or powder suitable for mixing with a liquid, for example water, milk or fruit juice at the point of use.

In a preferred embodiment, the composition comprises a solid bar comprising the ketone body or ketone body precursor including a hydroxybutyrate ester at a level of up to 95% weight of the composition, a flavouring and optionally an adsorbent. Preferably the hydroxybutyrate ester is present at a level of 30 to 95% by weight of the composition.

Suitable forms of liquid composition include for example a syrup, an emulsion and a suspension. Suitably, in the form of a syrup, the composition further may contain as carrier, for example, saccharose or saccharose with glycerol and/or mannitol and/or sorbitol. In the form of a suspension or emulsion, the composition may contain as a carrier, for example, a natural gum, agar, sodium alginate, pectin, methylcellulose, carboxymethylcellulose or polyvinyl alcohol.

The composition may be formulated to be consumed in combination with a balanced normal diet as a food or drink supplement or suitably may be formulated with further components to provide a significant component of an overall balanced diet of a user. Preferably the composition provides a fully balanced diet such that further nutritional intake is not required. A fully balanced diet allows use in conditions where other foodstuffs may not be available for any reason, for example for military use in the field, for use in exploration, terrestrial or celestial, for use in disaster areas such as famine or drought, in remote regions and in therapeutic treatment or preparative treatment prior to surgery and in enteral nutrition.

The composition may also be a food product, food supplement, dietary supplement, functional food or a nutraceutical or a component thereof.

A food product is an edible material composed primarily of one or more of the macronutrients protein, carbohydrate and fat, which is used in the body of an organism to sustain growth, repair damage, aid vital processes or furnish energy. A food product may also contain one or more micronutrients such as vitamins or minerals, or additional dietary ingredients such as flavourants and colourants. The term food product as used herein also covers a beverage.

Examples of food products into which the composition may be incorporated as an additive include snack bars, cereals, confectionery and probiotic formulations including yogurts. Examples of beverages include soft beverages, alcoholic beverages, energy beverages, dry drink mixes, nutritional beverages and herbal teas for infusion or herbal blends for decoction in water.

A nutraceutical is a food ingredient, food supplement or food product which is considered to provide a medical or health benefit, including the prevention and treatment of disease. In general a nutraceutical is specifically adapted to confer a particular health benefit on the consumer. A nutraceutical typically comprises a micronutrient such as a vitamin, mineral, herb or phytochemical at a higher level than would be found in a corresponding regular food product. That level is typically selected to optimise the intended health benefit of the nutraceutical when taken either as a single serving or as part of a diet regimen or course of nutritional therapy.

A functional food is a food that is marketed as providing a health benefit beyond that of supplying pure nutrition to the consumer. A functional food typically incorporates an ingredient such as a micronutrient as mentioned above, which confers a specific medical or physiological benefit other than a nutritional effect. A functional food typically carries a health claim on the packaging.

In a further aspect, the invention provides a process for the production of a composition according to the invention comprising the steps of combining the dry components with a liquid carrier to provide a processable composition, subjecting the processable composition to a mixing process, for example agglomeration, and/or a drying process, for example spray drying and fluid bed drying to provide a solid composition.

The liquid carrier suitably comprises the ketone body or the ketone body may be introduced before, during or after the mixing step.

Suitably the components may be combined in any desirable manner, for example by blending. The dry components may be added to the liquid carrier individually or in pre-mixed combinations of two or more dry components or all of the dry components may be mixed together prior to addition to the liquid carrier as desired. The liquid carrier suitably comprises water or the ketone body. In a preferred process, the dry components are blended together prior to addition to the liquid carrier. Where the liquid carrier comprises water, water may be removed at least in part during drying of the composition to provide a rehydratable solid particulate composition. As desired, the solid particulate composition may be provided as a solid for rehydration by the user at the point of use or may be provided as a liquid product for example by fully or partially hydrating the solid particulate composition to provide a paste or concentrate for subsequent dilution on use.

Preferably the solid composition is in a particulate form, for example a powder and granules and is free-flowing. The composition may be in a liquid form as desired, for example as a flowable liquid, viscous liquid or paste.

Compositions according to the invention may be used for any known application in which ketones are known or may provide a beneficial effect. The compositions may be used in a method of treatment of the human or animal body by therapy. In a preferred embodiment, the invention provides for the use of a composition according to the invention in one or more of the treatment or alleviation of fatigue, treatment of muscle impairment, as an appetite suppressant, in the treatment of cardiovascular conditions, improving cardiac efficiency, in improving brain metabolic efficiency, diabetes, cardiac impairment, hypopyrexia, hyperthyroidism, metabolic syndrome X, fever and infection and of conditions related to mitochondrial dysfunction and in treating a neurodegenerative disorder or cognitive dysfunction, for example Parkinson's disease and Alzheimer's disease or in reducing the effects of a neurodegenerative disorder.

The composition is especially beneficial in the prevention, treatment or alleviation of fatigue in combination with retaining or maintaining cognitive function and is especially advantageous for use in military applications where maintaining cognitive function is important under conditions of fatigue or stress.

The invention provides in further aspect a kit comprising a composition according to the invention and a ketone monitor and optionally instructions as to the level of composition to consume per unit body weight to achieve a pre-determined level of blood plasma ketone and a dosage regimen to maintain blood plasma ketone at the pre-determined level. The user suitably consumes the composition and may then periodically test their blood plasma ketone level to determine whether further ingestion of ketone is required to reach or to maintain the desired blood plasma ketone level.

The invention is described by reference to the following non-limiting examples.

EXAMPLE 1

A composition according to the invention was prepared by combining the components listed in Table 1 by mixing the dry components to produce a dry powder. The ketone body was then added to the dry composition by agglomeration to form a free-flowing powder. A 207 g dose of the composition was diluted with water to provide 960 ml single dose diluted liquid composition. 3 doses of this liquid composition were consumed per day to provide a calorific intake of 2400 Calories and providing an average intake of ketone of 150 g/day.

TABLE 1

| Ingredient | g/100 g |
| --- | --- |
| Ketone (UoR) D-β-hydroxybutyrate-R 1,3-butanediol monoester | 23.40 |
| Protein source: Full Cream Milk Powder (Lakeland) | 41.68 |
| Maltodextrin (Cerestar) | 14.00 |
| Granulated Sugar (Retail) | 11.20 |
| Fibre source: Nutriose FB06 (Roquette) (wheat derived) | 5.16 |
| Vitamin and Mineral Premix (Lycored) | 0.81 |
| Salt | 0.30 |
| Potassium Chloride (Lycored) | 0.30 |
| Strawberry & Cream Flavouring DD-688-924-1 (Givaudan) | 0.75 |
| Carrageenan CL20 FLX (Danisco) | 0.80 |
| Strawberry Red Colour 503268-0010-(Sensient) | 0.50 |
| Sucralose (Tate & Lyle) | 0.10 |
| Mono-Diglyceride (Danisco) | 1.00 |
| Total | 100.00 |

Mixing 100 g powder composition with 363 g water provides 463 g drink containing around 24 g of ketone. To gain 500 mg of ketone per kilogram of body weight per meal requires consumption of 9.65 g of the drink per kilogram body weight per meal, equating to 675 g of drink for a person of 70 kg mass. 463 g of drink contains 374 kcal of energy, equating to 545 kcal intake for a 675 g dose per meal for a person of 70 kg mass. In order to provide a 2400 kcal daily intake for a 70 kg person, requires a calorie intake of 800 kcal per meal for a 3 meal diet. A shortfall of 255 kcal per meal for a 70 kg person may be made up of solid food, equating to 3,64 kcal/kg of body weight per meal of solid food.

EXAMPLE 2

A composition according to the invention was prepared by combining the components listed in Table 2 by mixing the dry components to produce a dry powder. The ketone body was then added to the dry composition by agglomeration to form a free-flowing powder. A 207 g dose of the composition was diluted with water to provide 960 ml single dose diluted liquid composition. 3 doses of this liquid composition were consumed per day to provide a calorific intake of 2400 Calories and providing an average intake of ketone of 150 g/day.

TABLE 2

| Ingredient | g/100 g |
| --- | --- |
| Ketone (UoR) D-β-hydroxybutyrate-R 1,3-butanediol monoester | 23.40 |
| Protein source: Full Cream Milk Powder (Lakeland) | 41.58 |
| Maltodextrin (Cerestar) | 14.00 |
| Granulated Sugar (Retail) | 11.20 |
| Fibre source: Nutriose FB06 (Roquette) | 5.16 |
| Vitamin and Mineral Premix (Lycored) | 0.81 |
| Salt | 0.30 |
| Potassium Chloride (Lycored) | 0.30 |
| Instant Coffee Extract 878 (Givaudan) | 1.25 |
| Coffee Mocca Flavour PP-495-087-1 (Givaudan) | 0.10 |
| Carrageenan CL20 FLX (Danisco) | 0.80 |
| Sucralose (Tate & Lyle) | 0.10 |
| Mono-Diglyceride (Danisco) | 1.00 |
| Total | 100.00 |

EXAMPLE 3

A composition according to the invention was prepared by combining the components listed in Table 3 by mixing the dry components to produce a dry powder using a pilot scale twin shaft paddle mixer and sieved to 3 mm. The ketone body was then added to the dry composition by agglomeration to form a free-flowing powder. A 207 g dose of the composition was diluted with water to provide 960 ml single dose diluted liquid composition. 3 doses of this liquid composition were consumed per day to provide a calorific intake of 2400 Calories and providing an average intake of ketone of 150 g/day.

TABLE 3

Chocolate Beverage

| Supplier | Component | g/100 g |
| --- | --- | --- |
| | Ketone-D-β-hydroxybutyrate-R 1,3-butanediol monoester | 24.00 |
| Lakeland Dairies | Full Cream Milk Powder | 4.15 |
| Napier Brown | Skimmed Milk Powder | 30.25 |
| Volac | Whey Protein Isolate (Ultrawhey Instant 90) | 2.20 |
| Cargill | Maltodextrin 01915 | 10.00 |
| Retail | Granulated Sugar | 15.30 |
| Roquette | Nutriose FM06 | 5.16 |
| Lycored | Vitamin and Mineral Premix NUS850276 | 0.87 |
| Retail | Salt | 0.30 |
| Lycored | Potassium Chloride | 0.30 |
| Symrise | Chocolate Flavour (652167) | 2.50 |
| Symrise | Vanilla Cream/Mouthfeel (655064) | 0.25 |
| CP Kelco-S Black | Genuvisco Carrageenan CSM-2 | 1.50 |
| Overseel | Colouring (PG0447) | 0.60 |
| ADM Cocoa | Cocoa Powder D-11-Asol | 2.50 |
| Tate & Lyle | Sucralose | 0.12 |

EXAMPLE 4

A composition according to the invention was prepared by combining the components listed in Table 4 by mixing the dry components to produce a dry powder using a pilot scale twin shaft paddle mixer and sieved to 3 mm. The ketone body was then added to the dry composition by agglomeration to form a free-flowing powder. A 207 g dose of the composition was diluted with water to provide 960 ml single dose diluted liquid composition. 3 doses of this liquid composition were consumed per day to provide a calorific intake of 2400 Calories and providing an average intake of ketone of 150 g/day.

TABLE 4

Liquorice Beverage

| Supplier | Component | g/100 g |
| --- | --- | --- |
| | Ketone-D-β-hydroxybutyrate-R 1,3-butanediol monoester | 24.10 |
| Lakeland Dairies | Full Cream Milk Powder | 5.050 |
| Napier Brown | Skimmed Milk Powder | 33.050 |
| Volac | Whey Protein Isolate (Ultrawhey Instant 90) | 2.200 |
| Cargill | Maltodextrin 01915 | 10.250 |
| Retail | Granulated Sugar | 15.500 |
| Roquette | Nutriose FM06 | 5.160 |
| Lycored | Vitamin and Mineral Premix NUS850276 | 0.870 |
| Retail | Salt | 0.300 |
| Lycored | Potassium Chloride | 0.300 |
| Symrise | Chocolate Flavour (652167) | 0.450 |
| Symrise | Vanilla Cream/Mouthfeel (655064) | 0.300 |
| CP Kelco-S Black | Genuvisco Carrageenan CSM-2 | 1.500 |
| Overseel | Colouring (PG0447) | 0.600 |
| Sym rise | Liquorice Flavour (654120) | 0.250 |
| Tate & Lyle | Sucralose | 0.120 |

EXAMPLE 5

A composition according to the invention was prepared by combining the components listed in Table 5 by mixing the dry components to produce a dry powder using a pilot scale twin shaft paddle mixer and sieved to 3 mm. The ketone body was then added to the dry composition by agglomeration to form a free-flowing powder. A 207 g dose of the composition was diluted with water to provide 960 ml single dose diluted liquid composition. 3 doses of this liquid composition were consumed per day to provide a calorific intake of 2400 Calories and providing an average intake of ketone of 150 g/day.

TABLE 5

Coffee Beverage

| Supplier | Component | g/100 g |
|---|---|---|
| | Ketone-D-β-hydroxybutyrate-R 1,3-butanediol monoester | 23.75 |
| Lakeland Dairies | Full Cream Milk Powder | 5.00 |
| Napier Brown | Skimmed Milk Powder | 32.00 |
| Volac | Whey Protein Isolate (Ultrawhey Instant 90) | 2.20 |
| Cargill | Maltodextrin 01915 | 10.25 |
| Retail | Granulated Sugar | 15.50 |
| Roquette | Nutriose FM06 | 5.16 |
| Lycored | Vitamin and Mineral Premix NUS850276 | 0.87 |
| Retail | Salt | 0.30 |
| Lycored | Potassium Chloride | 0.30 |
| Symrise | Caramel (653281) | 0.10 |
| Symrise | Coffee Flavouring (201473) | 0.20 |
| Symrise | Vanilla Cream/Mouthfeel (655064) | 0.25 |
| CP Kelco-S Black | Genuvisco Carrageenan CSM-2 | 1.50 |
| Nestle (Retail) | Decaff Instant Coffee | 2.00 |
| Overseel | Colouring (OF1096) | 0.50 |
| Tate & Lyle | Sucralose | 0.12 |

EXAMPLE 6

A composition according to the invention was prepared by combining the components listed in Table 6 by mixing the dry components using a pilot scale twin shaft paddle mixer to produce a dry powder and sieved to 3 mm. The ketone body was then added to the dry composition by agglomeration to form a free-flowing powder. A 207 g dose of the composition was diluted with water to provide 960 ml single dose diluted liquid composition. 3 doses of this liquid composition were consumed per day to provide a calorific intake of 2400 Calories and providing an average intake of ketone of 150 g/day.

TABLE 6

Raspberry and Cranberry Beverage

| Supplier | Component | g/100 g |
|---|---|---|
| | Ketone-D-β-hydroxybutyrate-R 1,3-butanediol monoester | 24.10 |
| Lakeland Dairies | Full Cream Milk Powder | 5.00 |
| Napier Brown | Skimmed Milk Powder | 32.90 |
| Volac | Whey Protein Isolate (Ultrawhey Instant 90) | 2.20 |
| Cargill | Maltodextrin 01915 | 10.25 |
| Retail | Granulated Sugar | 15.50 |
| Roquette | Nutriose FM06 | 5.16 |
| Lycored | Vitamin and Mineral Premix NUS850276 | 0.87 |
| Retail | Salt | 0.30 |
| Lycored | Potassium Chloride | 0.30 |
| Symrise | Raspberry Flavouring (652742) | 0.45 |
| Symrise | Cranberry Flavouring (650722) | 0.30 |
| Symrise | Vanilla Cream/Mouthfeel (655064) | 0.25 |
| CP Kelco-S Black | Genuvisco Carrageenan CSM-2 | 1.50 |
| J.O. Sims | Cranberry Extract Powder (UPC 94502) | 0.50 |
| Sensient | Colouring (25:75 [503212:503268]) | 0.30 |
| Tate & Lyle | Sucralose | 0.12 |

EXAMPLE 7

Normal human subjects (n=18, 9 men and 9 women) were fed a single dose of D-β-hydroxybutyrate-R 1,3 butanediol monoester in a milk-based drink according to the invention. Their blood □-hydroxybutyrate concentrations were measured at intervals over the following 24 hours. The maximum plasma ketone concentrations reached for the 140, 357 or 714 mg/kg ketone ester doses were 0.23, 0.76 and 3.42 mM, respectively. These results are shown in FIG. 1.

EXAMPLE 8

Figure 2:
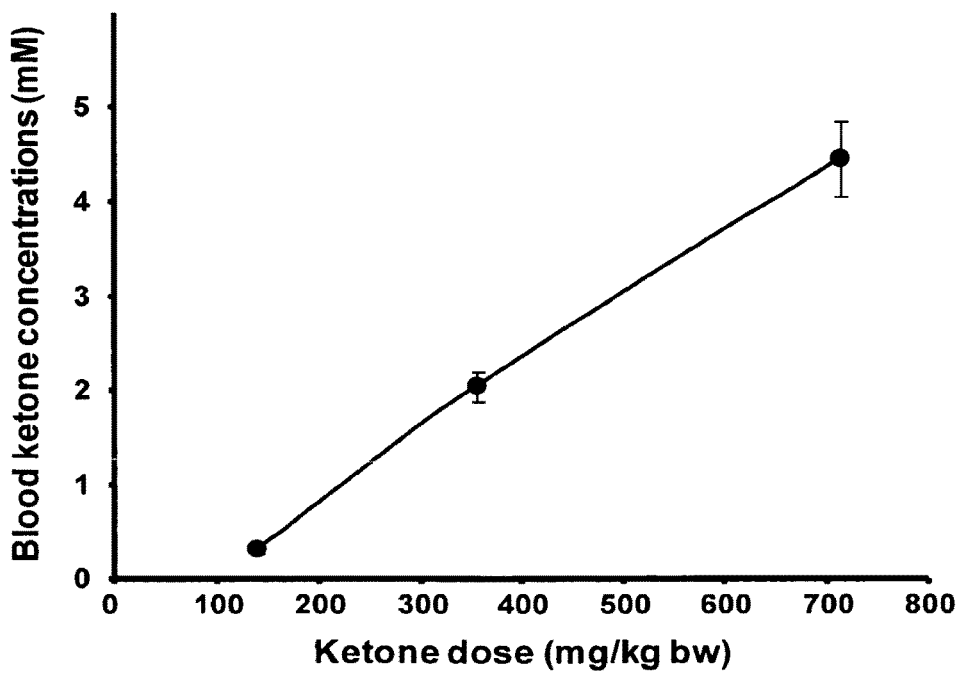
FIG. 2 is a graph depicting the maximum blood ketone concentration attained in human subjects after administration of a composition configured at one of three doses.

The maximum blood ketone concentrations in 18 subjects (n=6 per group) attained after a single drink of the formulation, 6 at 140 mg/kg body weight, 6 at 357 and 6 at 714 mg/kg bw were measured. The results are shown in FIG. 2 and provide an indication of the blood ketone concentration dependent on the dose consumed.

EXAMPLE 9

Compositions described in Example 3 (chocolate), Example 4 (coffee), Example 5 (liquorice) Example 6 (raspberry/cranberry) were tested in a blind taste test by 57 randomly selected volunteers. The volunteers were provided with samples of each of the compositions and asked to rank them from 1 to 10 as regards organoleptic acceptability (1 lowest, 10 highest) having regard to taste, odour, feel and colour. The results are shown below in Table 7 with each vertical group of four results, 1 for each flavour, representing the four rankings given by 1 volunteer for each of the drinks.

TABLE 7

| Flavour | | | | | | | | | | | | | | |
|---|---|---|---|---|---|---|---|---|---|---|---|---|---|---|
| Raspberry and Cranberry | 3 | 5 | 7 | 1 | 7 | 6 | 4 | 3 | 1 | 5 | 2 | 3 | 7 | 3 |
| Chocolate | 3 | 7 | 5 | 7 | 5 | 7 | 2 | 8 | 3 | 6 | 4 | 6 | 8 | 4 |
| Coffee | 3 | 5 | 4 | 1 | 1 | 6 | 3 | 9 | 4 | 4 | 5 | 2 | 4 | 6 |
| Liquorice | 3 | 2 | 6 | 4 | 4 | 3 | 3 | 5 | 3 | 1 | 2 | 1 | 2 | 5 |
| Raspberry and Cranberry | 5 | 2 | 2 | 4 | 4 | 1 | 6 | 2 | 4 | 6 | 4 | 1 | 1 | 1 |
| Chocolate | 7 | 4 | 4 | 2 | 5 | 2 | 6 | 5 | 2 | 4 | 3 | 7 | 3 | 2 |
| Coffee | 5 | 4 | 7 | 7 | 5 | 4 | 5 | 3 | 5 | 6 | 2 | 2 | 7 | 6 |
| Liquorice | 5 | 5 | 8 | 5 | 3 | 2 | 7 | 5 | 6 | 5 | 3 | 4 | 1 | 7 |
| Raspberry and Cranberry | 3 | 4 | 1 | 4 | 3 | 2 | 3 | 1 | 4 | 3 | 2 | 6 | 7 | 4 |
| Chocolate | 7 | 5 | 4 | 4 | 5 | 4 | 3 | 7 | 7 | 5 | 4 | 5 | 6 | 5 |
| Coffee | 4 | 5 | 8 | 5 | 6 | 2 | 4 | 5 | 5 | 7 | 1 | 4 | 4 | 2 |
| Liquorice | 2 | 7 | 2 | 7 | 6 | 3 | 2 | 6 | 6 | 1 | 2 | 7 | 2 | 1 |
| Raspberry and Cranberry | 2 | 3 | 7 | 4 | 3 | 3 | 4 | 3 | 3 | 4 | 2 | 5 | 1 | 2 | 7 |

TABLE 7-continued

| | | | | | | | | | | | | | | |
|---|---|---|---|---|---|---|---|---|---|---|---|---|---|---|
| Chocolate | 4 | 5 | 4 | 5 | 2 | 6 | 6 | 5 | 4 | 7 | 3 | 7 | 4 | 5 | 6 |
| Coffee | 3 | 5 | 4 | 3 | 3 | 8 | 7 | 7 | 4 | 7 | 3 | 6 | 4 | 5 | 6 |
| Liquorice | 1 | 6 | 2 | 1 | 2 | 1 | 3 | 6 | 5 | 8 | 1 | 6 | 1 | 6 | 8 |

The results were collated and the average ranks were as follows:

| | |
|---|---|
| Raspberry and cranberry | 3.50 |
| Chocolate | 4.82 |
| Coffee | 4.60 |
| Liquorice | 3.89 |

The data was grouped into rankings of 1-3, 4-7 and 8-10 and the results are shown in Table 8

TABLE 8

| | 1 to 3 | 4 to 7 | 8 to 10 | Total |
|---|---|---|---|---|
| Raspberry and Cranberry | 31 | 26 | 0 | 57 |
| Chocolate | 12 | 43 | 2 | 57 |
| Coffee | 15 | 39 | 3 | 57 |
| Liquorice | 29 | 25 | 3 | 57 |

Figure 3:
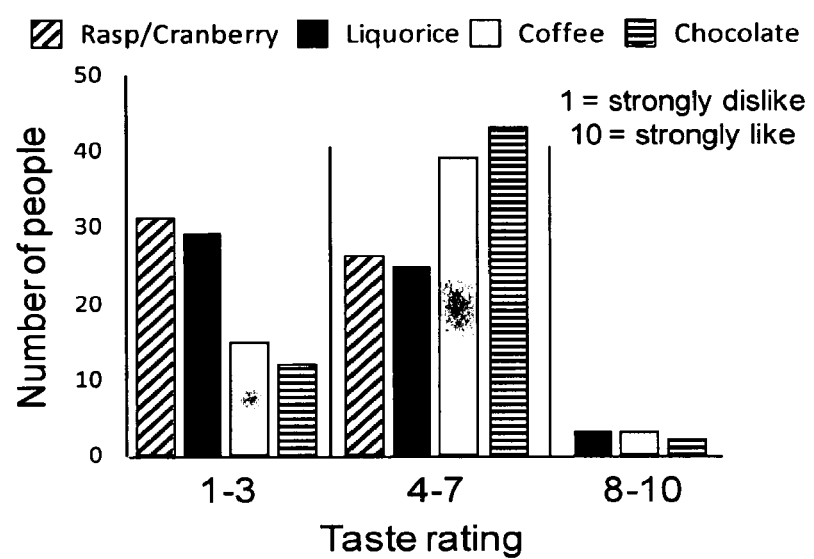
FIG. 3 is a bar graph depicting the results of a blind taste test of four differently flavoured compositions of the disclosure.

These results demonstrate that on average, the taste panel found chocolate and coffee to be preferable to the raspberry and cranberry and liquorice compositions although all were acceptable to a significant proportion of the panel. The grouped data from Table 8 is shown graphically in FIG. 3.

EXAMPLE 10

Compositions according to the invention comprising an adsorbent (Full Cream Milk Powder (Lakeland) or Skimmed Milk Powder (Napier)) when stored for a period of at least 1 week, preferably 1 month and preferably 3 months exhibit a progressively reduced perceived bitterness as compared to the freshly prepared product. By storing a composition of the invention containing an adsorbent for a period of time, the organoleptic properties of the composition may be improved.

The invention claimed is:

1. An organoleptically acceptable composition comprising a ketone body or a ketone body precursor including a hydroxybutyrate or derivative thereof, a bitter flavoring, and optionally one or more of a salt, vitamins and minerals; wherein the hydroxybutyrate or a derivative thereof is selected from a group consisting of a salt of (R)-3-hydroxybutyrate, an oligomer of (R)-3-hydroxybutyrate, an ester of an oligomer of (R)-3-hydroxybutyrate, and an ester of (R)-3-hydroxybutyrate.

2. The composition according to claim 1 wherein the hydroxybutyrate or a derivative thereof is present at a level of up to 50% weight of the composition.

3. The composition according to claim 1 wherein the composition is in the form of a drink, a solid or a gel.

4. The composition according to claim 1, wherein the composition comprises a hydroxybutyrate ester at a level of 30 to 95% by weight of the composition, a flavouring, and optionally an adsorbent.

5. The composition according to claim 1, wherein the composition is in liquid form and comprises the hydroxybutyrate or a derivative thereof, at a level of at least 1% by weight of the liquid composition.

6. The composition according to claim 5 in liquid form comprising water, milk or fruit juice as the liquid component.

7. The composition according to claim 1, further comprising at least two different ketone bodies each comprising a hydroxybutyrate or a derivative thereof.

8. The composition according to claim 1, wherein the ketone body or ketone body precursor comprises 3-hydroxybutyl-(R)-3-hydroxybutyrate.

9. The composition according to claim 8 wherein the 3-hydroxybutyl-(R)-3-hydroxybutyrate is in enantiomerically enriched form.

10. The composition according to claim 1, comprising a pharmaceutically acceptable adsorbent for the ketone body or a ketone body precursor including a hydroxybutyrate ester or a derivative thereof.

11. The composition according to claim 10 wherein the adsorbent is selected from a polymer hydrogel, a clathrate, a protein, and a carbohydrate.

12. A method of treatment of the human or animal body by therapy comprising administering to a subject a composition according to claim 1.

13. The method of claim 12 for treating cognitive dysfunction, diabetes, a cardiovascular condition, a condition related to mitochondrial dysfunction or a neurodegenerative disorder in which ketone bodies are known or may provide a beneficial effect; improving cardiac efficiency or brain metabolic efficiency; or reducing the effects of a neurodegenerative disorder.

14. The method of claim 12 for treating muscle impairment or fatigue or as an appetite suppressant.

15. The method of claim 12 for maintaining or improving cognitive function under fatigue or in reducing the adverse effects on cognitive function under fatigue.

16. The composition according to claim 1, wherein the composition comprises vitamins and minerals at a level such that at least 50% of the recommended daily allowance is provided on consumption of the composition over a 24-hour period.

17. A nutritional composition comprising a composition according to claim 1 and vitamins and minerals.

18. An organoleptically acceptable product comprising the composition of claim 1 and instructions for a dosage regime for consumption of the composition such that the user ingests at least 100 mg per kilogram of body weight of ketone body or ketone body precursor per day wherein upon consumption of the composition according to the instructions, provides a blood plasma ketone level of at least 0.1 mM.

19. The composition according to claim 1 further comprising a medium chain triglyceride (MCT) and/or L carnitine or an L carnitine derivative.

* * * * *